(12) United States Patent
Xing et al.

(10) Patent No.: US 11,566,259 B2
(45) Date of Patent: Jan. 31, 2023

(54) BROAD-SPECTRUM HIGH-RESISTANCE GENE PM21 RESISTANT TO WHEAT POWDERY MILDEW AS WELL AS EXPRESSION VECTOR AND USE THEREOF

(71) Applicant: NANJING AGRICULTURAL UNIVERSITY, Jiangsu (CN)

(72) Inventors: Liping Xing, Nanjing (CN); Aizhong Cao, Nanjing (CN); Ping Hu, Nanjing (CN); Jiaqian Liu, Nanjing (CN); Weihao Zhou, Nanjing (CN); Chaofan Cui, Nanjing (CN); Xiu'e Wang, Nanjing (CN); Ruiqi Zhang, Nanjing (CN); Shouzhong Zhang, Nanjing (CN); Peidu Chen, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 476 days.

(21) Appl. No.: 16/468,750

(22) PCT Filed: Nov. 22, 2017

(86) PCT No.: PCT/CN2017/112376
§ 371 (c)(1),
(2) Date: Jun. 12, 2019

(87) PCT Pub. No.: WO2018/113470
PCT Pub. Date: Jun. 28, 2018

(65) Prior Publication Data
US 2019/0367942 A1    Dec. 5, 2019

(30) Foreign Application Priority Data
Dec. 20, 2016 (CN) .................. CN201611187465

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

FOREIGN PATENT DOCUMENTS

| CN | 101748133 A | 6/2010 |
|---|---|---|
| CN | 104278028 A | 1/2015 |
| CN | 104877996 A | 9/2015 |
| CN | 105969778 A | 9/2016 |
| CN | 106754960 A | 5/2017 |
| WO | 2014/135682 A1 | 9/2014 |

OTHER PUBLICATIONS

McHale et al, 2006, Genome Biol. 7:212.*
Chen et al (1995, Theor. Appl. Genet. 91:1125-1128).*
Cao et al (2011, PNAS 108:7727-7732, including supprting information).*
Chen et al (2013, Mol. Breeding 31:477-484).*
Jiang et al (2013, J. Exp. Bot. 64:3735-3746).*
Lin, Z. S., et al., "Isolation and Molecular Analysis of Genes Stpk-V2 and Stpk-V3 Homologous To Powdery Mildew Resistance Gene Stpk-V in a Dasypyrum Villosum Accession and Its Derivatives", Plant Genetics, J. Appl. Genetics, vol. 54, pp. 417-426, (2013).
Ma, Yanxin, "Creation of Powdery Mildew Susceptible Mutant NM14 from Nannong 9918 and its Application in Resistant Mechanism Study", China Master's Theses Full-Text Database, Mar. 15, 2015.
Jefferson, Richard A. et al., "GUS Fusions: β-Glucuronidase As A Sensitive and Versatile Gene Fusion Marker in Higher Plants", The EMBO Journal, vol. 6, No. 13, pp. 3901-3907, (1987).
Christensen, Alan H. et al., "Ubiquitin Promoter-Based Vectors for High-Level Expression of Selectable and/or Screenable Marker Genes in Monocotyledonous Plants", Transgenic Research, vol. 5, pp. 213-218, (1996).
Chen, Peidu et al., "Radiation-Induced Translocations with Reduced Haynaldia Villosa Chromatin at the Pm21 Locus for Powdery Mildew Resistance in Wheat", Mol. Breeding, vol. 31, pp. 477-484, (2013).
Wang, Xiaoyun et al., "Establishment of An Effective Virus Induced Gene Silencing System With BSMV in Haynaldia Villosa", Mol. Biol. Rep., vol. 37, pp. 967-972, (2010).
Schweizer, Patrick et al., "A Transient Assay System for the Functional Assessment of Defense-Related Genes in Wheat", The American Phytopathological Society, MPMI, vol. 12, No. 8, pp. 647-654, (1999).
Feb. 23, 2018 Search Report issued in Chinese Patent Application No. PCT/CN2017/112376.

\* cited by examiner

*Primary Examiner* — Anne Kubelik
(74) *Attorney, Agent, or Firm* — Oliff PLC

(57) ABSTRACT

A CC-NBS-LRR gene NLR1-V encoded by the enduring and broad-spectrum gene Pm21 which is resistant to powdery mildew in the wheat-*Haynaldia villosa* 6VS/6AL translocation line in Nannong 9918, and an expression vector and use thereof. The ORF sequence of the NLR1-V gene having an NLR domain is as shown in SEQ ID NO: 1, and the encoded amino acid sequence is as shown in SEQ ID NO: 2.

8 Claims, 6 Drawing Sheets

Specification includes a Sequence Listing.

A

B

SEQUENCE LISTING

<160> NUMBER OF SEQ ID NOS: 18

<210> SEQ ID NO 1
<211> LENGTH: 2730
<212> TYPE: DNA
<213> ORGANISM: Haynaldia villosa

<400> SEQUENCE: 1

```
atgtctgcac cggtcgtcag cgccaccatg ggggcgatga acccctcat cggcaagctc      60 gccgcactga ttggtgacga gtacaagaaa ctcacagggg tgaggagaca ggcctccttc     120
ctcaaggatg agcttagcgc catgaaagct ctccttgaga agcttgagct catggatgaa     180
```

```
ctggatccct tggccaagaa ctggagggat tatgtccggg agatgtccta cgacatggag    240
aattgcattg atgacttcat gcagaccctt ggaggtgccg atgcaaagac gggctttatc    300
aagaagacgg ctaaacgtct caagacgttg cggaagcgtc atcgtattgc tgatcggatg    360
gaagagctca aggggcttgc tttgcaagca aatgaacgac gcatgaggta caagattgat    420
gattgcgcca attctaccaa tcgtgtcgtt cccatcgata ctcggatgtt ggcaatctac    480
aagcaggcaa cggggcttgt tggtattgat ggcccaaaga aagagcttgt aagtggttg     540 acagatactc aggaaaaact caaggtggtg gctattgttg datttggagg ccttggtaaa    600
actacacttg ccaaacaagt atatgatacg attggagggc aattcagctg taaaatattt    660
ttctctgttt ctcaaagacc tgatatgtca agcctccttc gtggtctcca atcggagctt    720
aatatggaag aggagttaac tcagcctcac gaggtgcaac acatcattgg ccgtcttaga    780
gaatatctca cacataagag gtaccttatt gttgttgatg acttgtggta tcaatcaaca    840
tggaatatca tgagttgtat ctttccagaa gtcgggaatg gaagtagagt aatagtaact    900
acacgagtgg aggatgtggc tatttgggca tgtcgtgatg accatgagtg tgtttataga    960
atggaacccc tcaaagaaca agactcaaga atgctgttct gtaatagagt atttggttcc   1020
ggatatgcct gtccactgcc gttaaaaaaa gtttcagatg aaattttgaa gaagtgtgga   1080
gggttgccac ttgcaattat cactatagct agtctattag caagtcgtca agcaagatca   1140
gacgagtgga gagcataag aaattgtttg gcgctaagc ttgccataaa ttccaccttg     1200
gaagagatga ggagtatact gaaccttagc tacatgcatc ttcctcttca tctccgtcca   1260
tgtctcctgt actttggcat gtatccgaaa gacaaaatta tcaggaggcg tgacatggtt   1320
ctacagtggg tagccgaagg cttttgtcaat aattctcatg gatctaatct agaggatgtt   1380
gcagagagtt atttcaatga gcttatcaat agaagtctaa ttcagcctgg agaatccata   1440
gatggaaaga ttgagtctta caaagtacac gatatgatgc ttgatttgat cctcagcaag   1500
tgtgcagaaa ataattttat aagtgtggca tataattgtg aagacgtggc aagaatgcat   1560
ggccgcgaat acaaggtccg tagattgtcc ttgacttcaa gtgctaacga tgcaacatca   1620
gaaaacattc atactagcat gcaacaaatt cgctcatttt catgctttgg agagcctaaa   1680
tacacacctc ctctttttgct atttaaaatac cttcgggtgc tagtgtttat atcctcagac   1740
gcgtttggtc cgatagtgga ccttactgct attggtcaat tgtttcagct aaggtatgtc   1800 aaggttctctg cttcatacgg aatagatttt cctaccgaat ttcgcaagct tgttcatttg   1860
gagacgctgg aagtatctgg tttttcacca agcatcccgt cagatattgt ttgcttgcca   1920
cggttatctc gtctgatcct tccgtgtctt acacgtcttc ctcaagggat tgccaacata   1980
aaatcattgc gtgcattgca ctgtatggag cacatctcgc tagaggatat taatggcctt   2040
ggcgagctga ccagtctgag ggagctgagg cttttacacta aaatggtggc gggtgaagtt   2100
gatgctttgg tatccctaat tggaaagctc catgacctaa aatacctcgc ggtctctgtt   2160
gagtcttcta acatcattg cgacccgttg tactcattat caaaccctcc tctccatatc    2220
gaggaacttg atctgtacgg gtggacactg aagagagttc ccacatggat tggtgacctc   2280
catttccttc ggatcctgga tttgtgtgtc tacaacttgt tgaacgacga ggttcatgtt   2340
gtgggaaatc ttccctgcct cgtccatctg cgtctaaggg tgttcgctga aggcggggcc   2400
gtaatctgca cgggcttatt ccaagtcctg aaagtcctte gtctcttctc tcatgatgtg   2460
gaagacatgc agtttcagat agggctaatg cccagcctgc gacagctcac tctagaagta   2520
aataatggct ggggtggtgc tgtgcctcga ggcatggagc acctattggc cctcgatcac   2580
```

-continued

```
atctctgtat tgccagacg cggcgtcaat caccgtgatg tcgagtctgc cttcagaagc    2640
gtcttcgatg tgcacccaag acaaccttcc ttagaaataa tacctgatgt tcccctcagt    2700
tctatgaatg tggtcccagt tttactttaa                                    2730
```

<210> SEQ ID NO 2
<211> LENGTH: 909
<212> TYPE: PRT
<213> ORGANISM: Haynaldia villosa

<400> SEQUENCE: 2

```
Met Ser Ala Pro Val Val Ser Ala Thr Met Gly Ala Met Asn Pro Leu
1               5                   10                  15

Ile Gly Lys Leu Ala Ala Leu Ile Gly Asp Glu Tyr Lys Lys Leu Thr
            20                  25                  30

Gly Val Arg Arg Gln Ala Ser Phe Leu Lys Asp Glu Leu Ser Ala Met
        35                  40                  45

Lys Ala Leu Leu Glu Lys Leu Glu Leu Met Asp Glu Leu Asp Pro Leu
    50                  55                  60

Ala Lys Asn Trp Arg Asp Tyr Val Arg Glu Met Ser Tyr Asp Met Glu
65                  70                  75                  80

Asn Cys Ile Asp Asp Phe Met Arg Asp Leu Gly Gly Ala Asp Ala Lys
                85                  90                  95

Thr Gly Phe Ile Lys Lys Thr Ala Lys Arg Leu Lys Thr Leu Arg Lys
            100                 105                 110

Arg His Arg Ile Ala Asp Arg Met Glu Glu Leu Lys Gly Leu Ala Leu
        115                 120                 125

Gln Ala Asn Glu Arg Arg Met Arg Tyr Lys Ile Asp Asp Cys Ala Asn
    130                 135                 140

Ser Thr Asn Arg Val Val Pro Ile Asp Thr Arg Met Leu Ala Ile Tyr
145                 150                 155                 160

Lys Gln Ala Thr Gly Leu Val Gly Ile Asp Gly Pro Lys Lys Glu Leu
                165                 170                 175

Val Ser Trp Leu Thr Asp Thr Gln Glu Lys Leu Lys Val Val Ala Ile
            180                 185                 190

Val Gly Phe Gly Gly Leu Gly Lys Thr Thr Leu Ala Lys Gln Val Tyr
        195                 200                 205

Asp Thr Ile Gly Gly Gln Phe Ser Cys Lys Ile Phe Phe Ser Val Ser
    210                 215                 220

Gln Arg Pro Asp Met Ser Ser Leu Leu Arg Gly Leu Gln Ser Glu Leu
225                 230                 235                 240

Asn Met Glu Glu Glu Leu Thr Gln Pro His Glu Val Gln His Ile Ile
                245                 250                 255

Gly Arg Leu Arg Glu Tyr Leu Thr His Lys Arg Tyr Leu Ile Val Val
            260                 265                 270

Asp Asp Leu Trp Tyr Gln Ser Thr Trp Asn Ile Met Ser Cys Ile Phe
        275                 280                 285

Pro Glu Val Gly Asn Gly Ser Arg Val Ile Val Thr Thr Arg Val Glu
    290                 295                 300

Asp Val Ala Ile Trp Ala Cys Arg Asp His Glu Cys Val Tyr Arg
305                 310                 315                 320

Met Glu Pro Leu Lys Glu Gln Asp Ser Arg Met Leu Phe Cys Asn Arg
                325                 330                 335
```

```
Val Phe Gly Ser Gly Tyr Ala Cys Pro Leu Pro Leu Lys Lys Val Ser
            340                 345                 350

Asp Glu Ile Leu Lys Lys Cys Gly Gly Leu Pro Leu Ala Ile Ile Thr
            355                 360                 365

Ile Ala Ser Leu Leu Ala Ser Arg Gln Ala Arg Ser Asp Glu Trp Glu
370                 375                 380

Ser Ile Arg Asn Cys Leu Gly Ala Lys Leu Ala Ile Asn Ser Thr Leu
385                 390                 395                 400

Glu Glu Met Arg Ser Ile Leu Asn Leu Ser Tyr Met His Leu Pro Leu
            405                 410                 415

His Leu Arg Pro Cys Leu Leu Tyr Phe Gly Met Tyr Pro Glu Asp Lys
            420                 425                 430

Ile Ile Arg Arg Arg Asp Met Val Leu Gln Trp Val Ala Glu Gly Phe
            435                 440                 445

Val Asn Asn Ser His Gly Ser Asn Leu Glu Asp Val Ala Glu Ser Tyr
            450                 455                 460

Phe Asn Glu Leu Ile Asn Arg Ser Leu Ile Gln Pro Gly Glu Ser Ile
465                 470                 475                 480

Asp Gly Lys Ile Glu Ser Tyr Lys Val His Asp Met Met Leu Asp Leu
            485                 490                 495

Ile Leu Ser Lys Cys Ala Glu Asn Asn Phe Ile Ser Val Ala Tyr Asn
            500                 505                 510

Cys Glu Asp Val Ala Arg Met His Gly Arg Glu Tyr Lys Val Arg Arg
            515                 520                 525

Leu Ser Leu Thr Ser Ser Ala Asn Asp Ala Thr Ser Glu Asn Ile His
            530                 535                 540

Thr Ser Met Gln Gln Ile Arg Ser Phe Ser Cys Phe Gly Glu Pro Lys
545                 550                 555                 560

Tyr Thr Pro Pro Leu Leu Leu Phe Lys Tyr Leu Arg Val Leu Val Phe
            565                 570                 575

Ile Ser Ser Asp Ala Phe Gly Pro Ile Val Asp Leu Thr Ala Ile Gly
            580                 585                 590

Gln Leu Phe Gln Leu Arg Tyr Val Lys Val Ser Ala Ser Tyr Gly Ile
            595                 600                 605

Asp Phe Pro Thr Glu Phe Arg Lys Leu Val His Leu Glu Thr Leu Glu
            610                 615                 620

Val Ser Gly Phe Ser Pro Ser Ile Pro Ser Asp Ile Val Cys Leu Pro
625                 630                 635                 640

Arg Leu Ser Arg Leu Ile Leu Pro Cys Leu Thr Arg Leu Pro Gln Gly
            645                 650                 655

Ile Ala Asn Ile Lys Ser Leu Arg Ala Leu His Cys Met Glu His Ile
            660                 665                 670

Ser Leu Glu Asp Ile Asn Gly Leu Gly Glu Leu Thr Ser Leu Arg Glu
            675                 680                 685

Leu Arg Leu Tyr Thr Lys Met Val Ala Gly Glu Val Asp Ala Leu Val
            690                 695                 700

Ser Leu Ile Gly Lys Leu His Asp Leu Lys Tyr Leu Ala Val Ser Val
705                 710                 715                 720

Glu Ser Ser Lys His His Cys Asp Pro Leu Tyr Ser Leu Ser Asn Pro
            725                 730                 735

Pro Leu His Ile Glu Glu Leu Asp Leu Tyr Gly Trp Thr Leu Lys Arg
            740                 745                 750
```

-continued

Val Pro Thr Trp Ile Gly Asp Leu His Phe Leu Arg Ile Leu Asp Leu
        755                 760                 765

Cys Val Tyr Asn Leu Leu Asn Asp Glu Val His Val Val Gly Asn Leu
        770                 775                 780

Pro Cys Leu Val His Leu Arg Leu Arg Val Phe Ala Glu Gly Gly Ala
785                 790                 795                 800

Val Ile Cys Thr Gly Leu Phe Gln Val Leu Lys Val Leu Arg Leu Phe
            805                 810                 815

Ser His Asp Val Glu Asp Met Gln Phe Gln Ile Gly Leu Met Pro Ser
            820                 825                 830

Leu Arg Gln Leu Thr Leu Glu Val Asn Asn Gly Trp Gly Gly Ala Val
        835                 840                 845

Pro Arg Gly Met Glu His Leu Leu Ala Leu Asp His Ile Ser Val Phe
850                 855                 860

Ala Arg Arg Gly Val Asn His Arg Asp Val Glu Ser Ala Phe Arg Ser
865                 870                 875                 880

Val Phe Asp Val His Pro Arg Gln Pro Ser Leu Glu Ile Ile Pro Asp
            885                 890                 895

Val Pro Leu Ser Ser Met Asn Val Val Pro Val Leu Leu
        900                 905

<210> SEQ ID NO 3
<211> LENGTH: 23
<212> TYPE: DNA
<213> ORGANISM: Artificial Sequence
<220> FEATURE:
<223> OTHER INFORMATION: Synthetic construct

<400> SEQUENCE: 3
attgagatgt ctgcaccggt cgt                                    23

<210> SEQ ID NO 4
<211> LENGTH: 26
<212> TYPE: DNA
<213> ORGANISM: Artificial Sequence
<220> FEATURE:
<223> OTHER INFORMATION: Synthetic construct

<400> SEQUENCE: 4
ctctcttcgt tacataatgt agtgcc                                 26

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
acgggcttat tccaagtcct                                        20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
acgcttctga aggcagactc                                        20

```
<210> SEQ ID NO 7
<211> LENGTH: 40
<212> TYPE: DNA
<213> ORGANISM: Artificial Sequence
<220> FEATURE:
<223> OTHER INFORMATION: Synthetic construct

<400> SEQUENCE: 7
ggagagaaca cggggatcc atgtctgcac cggtcgtcag                              40

<210> SEQ ID NO 8
<211> LENGTH: 50
<212> TYPE: DNA
<213> ORGANISM: Artificial Sequence
<220> FEATURE:
<223> OTHER INFORMATION: Synthetic construct

<400> SEQUENCE: 8
aacgtcgtat gggtaaggcc tttaaagtaa aactgggacc acattcatag                  50

<210> SEQ ID NO 9
<211> LENGTH: 35
<212> TYPE: DNA
<213> ORGANISM: Artificial Sequence
<220> FEATURE:
<223> OTHER INFORMATION: Synthetic construct

<400> SEQUENCE: 9
gattacgcca agcttgggtc cgtcgactat ctctg                                  35

<210> SEQ ID NO 10
<211> LENGTH: 34
<212> TYPE: DNA
<213> ORGANISM: Artificial Sequence
<220> FEATURE:
<223> OTHER INFORMATION: Synthetic construct

<400> SEQUENCE: 10
accggtgcag acatctcaat gccgaggctc cttc                                   34

<210> SEQ ID NO 11
<211> LENGTH: 31
<212> TYPE: DNA
<213> ORGANISM: Artificial Sequence
<220> FEATURE:
<223> OTHER INFORMATION: Synthetic construct

<400> SEQUENCE: 11
tcggcattga gatgtctgca ccggtcgtca g                                      31

<210> SEQ ID NO 12
<211> LENGTH: 47
<212> TYPE: DNA
<213> ORGANISM: Artificial Sequence
<220> FEATURE:
<223> OTHER INFORMATION: Synthetic construct

<400> SEQUENCE: 12
aacgtcgtat gggtaaggcc taagtaaaac tgggaccaca ttcatag                     47

<210> SEQ ID NO 13
<211> LENGTH: 29
<212> TYPE: DNA
<213> ORGANISM: Artificial Sequence
<220> FEATURE:
<223> OTHER INFORMATION: Synthetic construct
```

```
<400> SEQUENCE: 13
gctgctagcc gagtggagga tgtggctat                                29

<210> SEQ ID NO 14
<211> LENGTH: 29
<212> TYPE: DNA
<213> ORGANISM: Artificial Sequence
<220> FEATURE:
<223> OTHER INFORMATION: Synthetic construct

<400> SEQUENCE: 14
gctgctagcc gtctgatctt gcttgacga                                29

<210> SEQ ID NO 15
<211> LENGTH: 29
<212> TYPE: DNA
<213> ORGANISM: Artificial Sequence
<220> FEATURE:
<223> OTHER INFORMATION: Synthetic construct

<400> SEQUENCE: 15
gctgctagcc tgagggagct gaggcttta                                29

<210> SEQ ID NO 16
<211> LENGTH: 29
<212> TYPE: DNA
<213> ORGANISM: Artificial Sequence
<220> FEATURE:
<223> OTHER INFORMATION: Synthetic construct

<400> SEQUENCE: 16
gctgctagcc caatccatgt gggaactct                                29

<210> SEQ ID NO 17
<211> LENGTH: 15
<212> TYPE: DNA
<213> ORGANISM: Artificial Sequence
<220> FEATURE:
<223> OTHER INFORMATION: Synthetic construct

<400> SEQUENCE: 17
gattacgcca agctt                                               15

<210> SEQ ID NO 18
<211> LENGTH: 21
<212> TYPE: DNA
<213> ORGANISM: Artificial Sequence
<220> FEATURE:
<223> OTHER INFORMATION: Synthetic construct

<400> SEQUENCE: 18
aacgtcgtat gggtaaggcc t                                        21
```

BROAD-SPECTRUM HIGH-RESISTANCE GENE PM21 RESISTANT TO WHEAT POWDERY MILDEW AS WELL AS EXPRESSION VECTOR AND USE THEREOF

BACKGROUND

Technical Field

The present invention falls within the field of genetic engineering, and discloses a CC-NBS-LRR gene NLR1-V encoded by the broad-spectrum gene Pm21 which is resistant to powdery mildew in the wheat (*Triticum aestivum*)-*Haynaldia villosa* translocation line 6VS/6AL in Nannong 9918, and an expression vector and use thereof.

Related Art

The whole growth period of wheat is endangered by a variety of pests and diseases, wherein wheat powdery mildew caused by infection by *Bluneria graninis* f. sp. *tritici*, Bgt is one of the most serious fungal diseases in wheat. Due to the multiple physiological minor species and rapid virulence variation of the Bgt, once a new virulence minor species is generated or a minor species population is changed, it will lead to a large outbreak of wheat powdery mildew, which will have disastrous consequences for agricultural production. The discovery and utilization of broad-spectrum and enduring disease-resistant genes are of great significance for the prevention and control of powdery mildew.

A powdery mildew resistant gene Pm21 carried by *Haynaldia villosa* (2n=2×=14. VV) has broad-spectrum and high-resistance characteristics to wheat powdery mildew, and the gene is located on the short arm of the 6V chromosome. The Cytogenetics Institute of Nanjing Agricultural University (CINAU) used the tetraploid turgidumto hybridize with the diploid *Haynaldia villosa*, then backcross with wheat for several generations, then selected the wheat-*Haynaldia villosa* translocation line 6VS/6AL, and introduced 6VS containing the Pm21 gene into wheat. The wheat-*Haynaldia villosa* translocation line 6VS/6AL has been planted in powdery mildew areas for many years since it entered domestic breeding and was utilized in 1994, showing broad-spectrum and high-resistance characteristics to powdery mildew. Using the wheat-*Haynaldia villosa* translocation line 6VS/6AL as a parent, a batch of new wheat varieties with high resistance to powdery mildew have been selected for breeding, and Nannong 9918 is one of the varieties bred, Pm21 has been widely used in breeding. Cloning the Pm2/gene and studying its broad-spectrum resistance mechanisms are of great significance to the use of genetic engineering methods to breed wheat varieties with broad-spectrum resistance to powdery mildew.

SUMMARY

The present invention is directed to the defects of the prior art and provides a CC-NBS-LRR gene NLR1-V encoded by the broad-spectrum gene Pm21 which is resistant to powdery mildew, and an expression vector and use thereof.

The object of the present invention may be achieved by the following technical solutions of the CC-NBS-LRR gene NLR1-V encoded by the broad-spectrum gene Pm2/which is resistant to powdery mildew, from wheat cv. Nannong 9918 and having the nucleotide sequence of SEQ ID NO: 1:

the protein of the CC-NBS-LRR gene NLR1-V being NLR1-V, and having the amino acid sequence of SEQ ID NO: 2;

the recombinant expression vectors containing the CC-NBS-LRR gene NLR1-V are pBI220: 35S-NLR1-V and pBI220: Native Promoter-NLR1-V:

the recombinant expression vector of the CC-NBS-LRR gene NLR1-V being preferably obtained by using pBI220 as a starting vector, inserting the NLR1-V gene into the BamHI and StuI restriction sites of pBI220, and placing NLR1-V under a 35S promoter to obtain the pBI220: 35S-NLR1-V;

the recombinant expression vector of the CC-NBS-LRR gene NLR1-V being preferably obtained by using pBI220 as a starting vector, and placing the NLR1-V under the promotion of the native promoter by a homologous recombination method to obtain pBI220: Native Promoter-NLR1-V;

use of the NLR gene NLR1-V in the construction of wheat varieties resistant to powdery mildew; and use of the recombinant expression vectors of the NLR gene NLR1-V in the construction of wheat varieties resistant to powdery mildew.

Beneficial Effects

The present invention clones to obtain the broad-spectrum gene which is resistant to powdery mildew from the 6VS chromosome arm of wheat-*Haynaldia villosa* translocation line 6VS/6AL in Nannong 9918. NLR1-V gene is a CC-NBS-LRR gene, which encodes the protein NLR1-V. When the gene is inserted into the expression vector pBI220, the expression vectors pBI220: 35S-NLR1-V and pBI220: Native Promoter-NLR1-V of the gene are obtained. When the above recombinant expression vectors are introduced into susceptible wheat varieties, the resistance of powdery mildew susceptible wheat varieties to powdery mildew is improved. The expression vectors pBI220: 35S-NLR1-V and pBI220: Native Promoter-NLR1-V are used in genetic engineering breeding, and wheat germplasm with resistance to powdery mildew is obtained by introducing the expression vectors into a wheat variety susceptible to powdery mildew.

Part A illustrates vector map of pBI220: 35S-NLR1-V; Part B illustrates vector map of pBI220: Native Promoter-NLR1-V.

Figure 4:
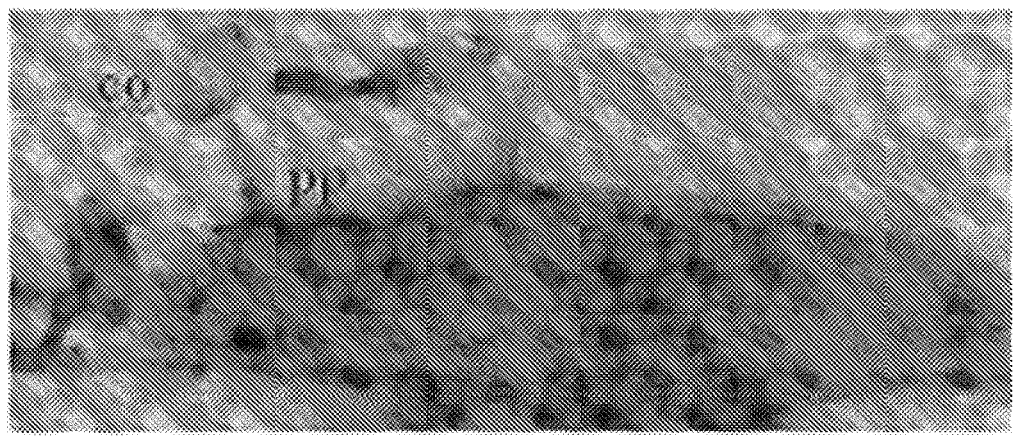
Figure 4:
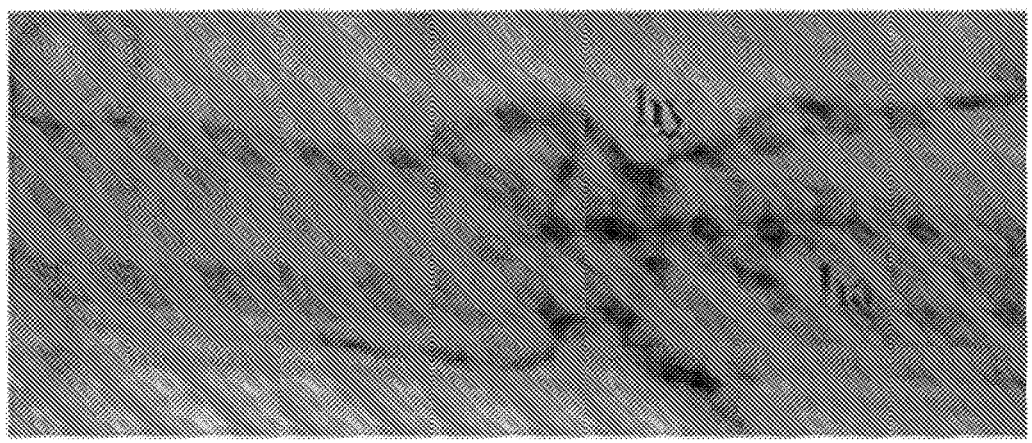

FIG. 4 illustrates epidermal cells expressing GUS genes and interacting with Bgt.

Part A illustrates that Bgt infecting the GUS-expressing epidermal cells does not form haustoria; Part B illustrates that Bgt infecting the GUS-expressing epidermal cells forms haustoria; among them, co refers to conidia, pp refers to penetration peg, ha refers to haustoria, and hy refers to hyphae.

Figure 5:
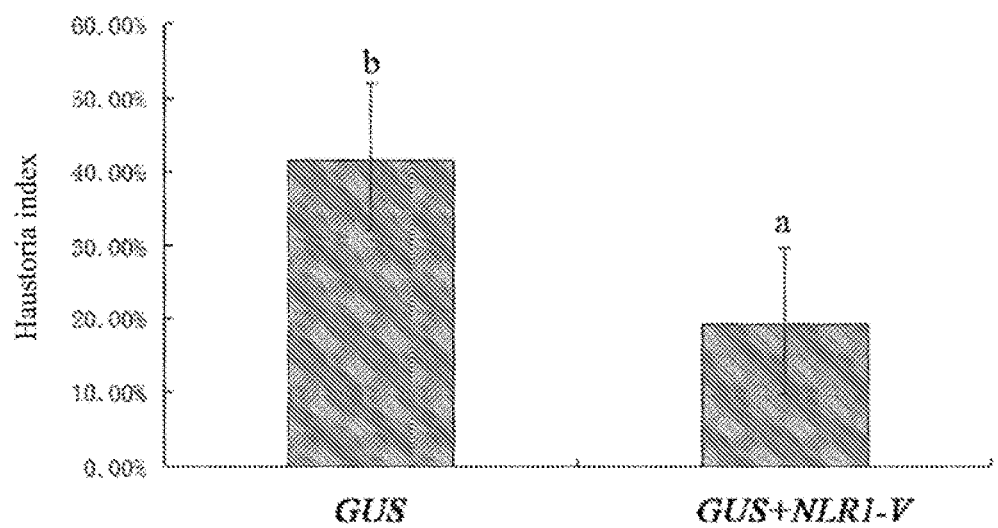

FIG. 5 illustrates using transient expression to study the effect of NLR1-V gene on the formation of haustoria and the resistance to powdery mildew.

Figure 6:
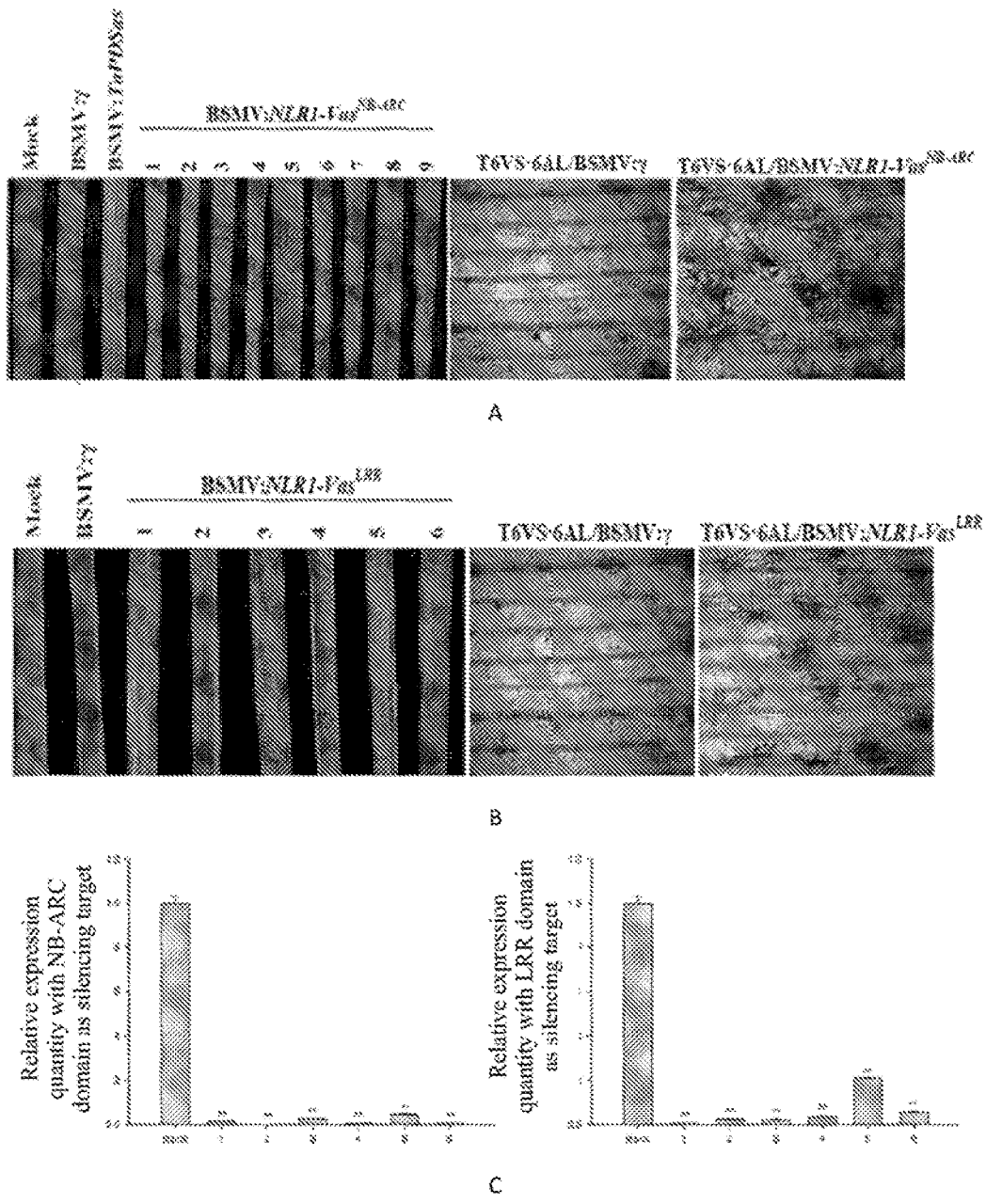

FIG. 6 illustrates NLR1-V gene silencing leads to compromised resistance of Nannong 9918.

Part A illustrates gene silencing effect map with NB-ARC domain as a silencing target; Part B illustrates gene silencing effect map with LRR domain as a silencing target; Part C illustrates detection of gene silencing efficiency.

Figure 7:
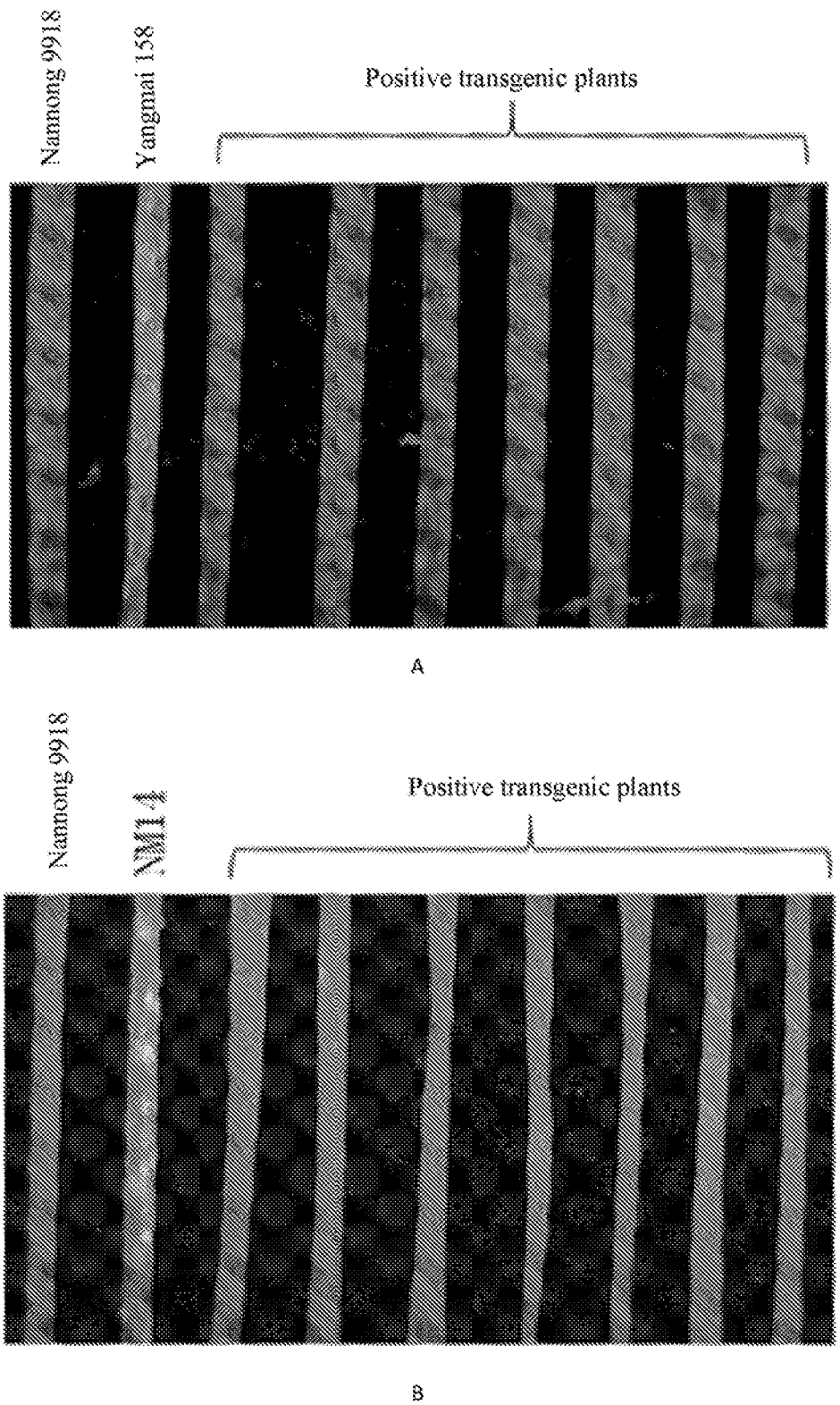

FIG. 7 illustrates that NLR1-V gene introduced into powdery mildew susceptible wheat varieties can improve their resistance to powdery mildew.

Part A illustrates identification of disease resistance of transgenic positive plants with Yangmai 158 as a transforming receptor. Part B illustrates identification of disease resistance of transgenic positive plants with a susceptible mutant as a transforming receptor.

DETAILED DESCRIPTION

Embodiment 1 Cloning of CC-NBS-LRR Gene NLR1-V Encoded by the Broad-Spectrum Gene Pm21 which is Resistant to Powdery Mildew in the Wheat-*Haynaldia villosa* 6VS/6AL Translocation Line Cv. Nannong 9918

Wheat-*Haynaldia villosa* 6VS/6AL translocation line cv. Nannong 9918, bred by the Cytogenetics Institute of Nanjing Agricultural University, is a wheat variety containing a broad-spectrum gene Pm21 which is resistant to powdery mildew. (Public, Chen Peidu, Zhang Shouzhong, Wang Xiu'e, Wang Suling, Zhou Bo, Feng Yigao, Liu Dajun. New powdery mildew resistant high-yield wheat variety Nannong 9918. Journal of Nanjing Agricultural University, 2002. 25(4):1438-1444). A number of 6VS specific markers have been developed on the 6VS of Nannong 9918 in the early stage. Further, the small-fragment insertion translocation line NAU418 is used to define Pm21 between 6EST258 and CINAU15, and there are 6EST243 and 6EST238 markers in the chromosome region where the Pm21 is located. (Public. Radiation-induced translocations with reduced *Haynaldia villosa* chromatin at the Pm21 locus for powdery mildew resistance in wheat. Molecular breeding, 2013, 31:477-484).

Blastn alignment analysis was performed on sequences of 6EST258. CINAU15, 6EST243 and 6EST238 and the sequence databases of rice (http://rice.plantbiology.msu.edu), barley (http://webblast.ipk-gatersleben.de/barley/viroblast.php), and *Brachypodium distachyon* (http://plants.ensembl.org/Brachypodium_distachyon/Info/index), and the sequences located in the chromosome regions of 6EST258 and CINAU15 in rice, barley and *Brachypodium distachyon* were extracted respectively.

Figure 1:
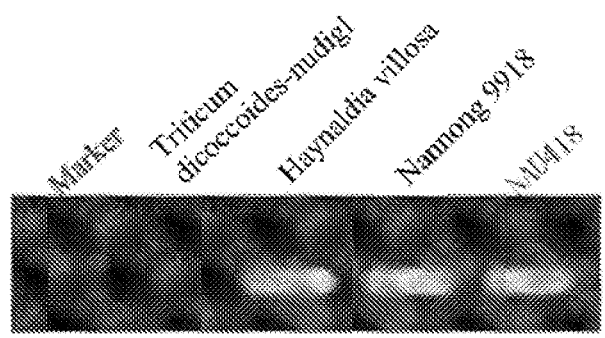
FIG. 1 illustrates that NLR1-V is located in the Pm21 segment of the small-fragment NAU418 translocation line of wheat-*Haynaldia villosa*.

Based on the discovery that most of the disease-resistant genes cloned encode the CC-NBS-LRR gene, a full-length CC-NBS-LRR gene database of *Haynaldia villosa* was obtained by R gene enrichment sequencing. The full-length CC-NBS-LRR gene of *Haynaldia villosa* was obtained by sequencing and assembling was compared with the barley genome, and the CC-NBS-LRR gene was electronically localized. A total of 45 CC-NBS-LRR genes co-linear with 6H were screened, wherein five of these genes were located in the chromosome segment of Pm21 defined by NAU418. The five genes were physically localized, and the results showed that the five genes (NLR1-V, NLR2-V, NLR3-V, NLR4-V and NLR5-V) were truly located in the segment of Pm21 defined by NAU418 (FIG. 1). The full-length cDNA amplification primers were designed based on the sequenced and assembled NLR1-V, NLR2-V, NLR3-V, NLR4-V and NLR5-V. The five genes were amplified and cloned in Nannong 9918 and its susceptible mutant NM14 respectively (Public: Creation of Nannong 9918 powdery mildew susceptible mutant NM14 and application thereof in disease resistance mechanism research, Master Thesis. Ma Yanxin, 2013, Nanjing Agricultural University). An alignment revealed that only NLR1-V has sequence difference in Nannong 9918 and its susceptible mutant NM14, and the other four genes have identical sequences in Nannong 9918 and its susceptible mutant NM14. Based on the above results, NLR1-V was identified as a candidate gene for the Pm21 gene. An amplification and cloning process of NLR1-V in Nannong 9918 cDNA samples induced by powdery mildew was performed as discussed below.

The specific process was as follows: (1) germinating the seeds of the powdery mildew resistant wheat Nannong 9918 in a culture dish, and then transplanting to pots after white sprouts appears; inoculating the seedlings at the first leaf stage with the spores of powdery mildew collected from powdery mildew susceptible wheat for induction, and taking samples at different time periods of inoculation (0 h, 1 h, 6 h, 12 h, 24 h); separately extracting RNA (extracted with a Trizol reagent from Invitrogen) and reversely transcribing into cDNA samples (carried out with AMV reverse transcriptase from Takara); (2) using the cDNA of Nannong 9918 induced by powdery mildew for 24 h as a template, and performing RT-PCR by using NLR1-V gene primers P1 (ATTGAGATGTCTGCACCGGTCGT, SEQ ID NO: 3) and P2 (CTCTCTTCGTTACATAATGTAGTGCC, SEQ ID NO: 4) as primers to obtain the full-length cDNA fragment SEQ ID NO: 1 of the NLR1-V gene. By sequencing and aligning the gene fragment, the gene was found to be a CC-NBS-LRR gene, and named as NLR1-V. Bioinformatic analysis of the NLR1-V revealed that the ORF (open reading frame) was 2730 bp, and its nucleotide sequence is as shown in SEQ ID NO: 1, which encodes 909 amino acids, and the amino acid sequence is shown in SEQ ID NO: 2.

Embodiment 2 Expression of NLR1-V Gene Induced by Powdery Mildew in the Wheat-*Haynaldia villosa* 6VS/6AL Translocation Line Cv. Nannong 9918

Figure 2:
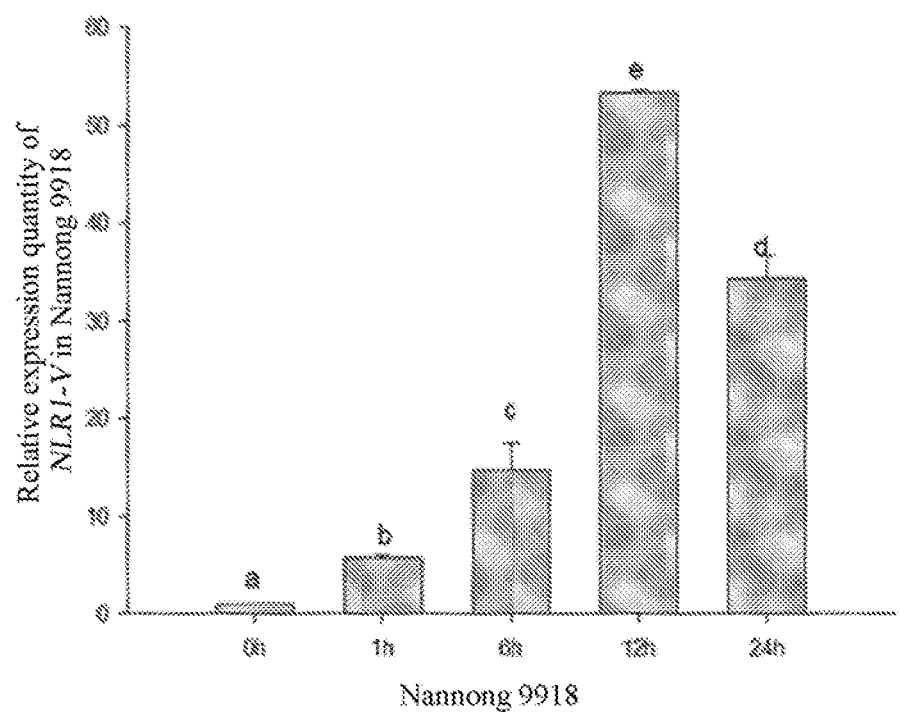
FIG. 2 illustrates that NLR1-V is induced and expressed by Bgt in the powdery mildew resistant Nannong 9918.

The cDNA samples induced by powdery mildew at different time periods of the wheat-*Haynaldia villosa* 6VS/6AL translocation line cv. Nannong 9918 were used as templates, and primers P3 (ACGGGCTTATTCCAAGTCCT. SEQ ID NO: 5) and P4 (ACGCTTCTGAAGGCAGACTC, SEQ ID NO: 6) designed according to NLR1-V were used as primers for carrying out Q-PCR analysis. A PCR procedure was amplifying PCR reaction on a real-time fluorescent quantitative PCR instrument (MyIQ, Bio-Rad. USA) and detecting fluorescence. A 20 uL PCR reaction system contained 10 uL of 2×SYBR Green PCR Master Mix, 0.5 μM of primers P3 and P4, and 2 uL of inverse transcription cDNA templates. The amplification parameters were 95° C. for 10 minutes, then 95° C. for 15 seconds, 60° C. for 30 seconds, and 72° C. for 1 minute for a total of 40 cycles. After the reaction was completed, the measurement of a melting curve was carried out. Detection of gene expression levels was analyzed by using the MyiQ system software. The results showed that in Nannong 9918, NLR1-V expression is induced to up-regulate by Bgt in the wheat-*Haynaldia villosa* 6VS/6AL translocation line cv. Nannong 9918, the expression level was the highest at 12 h. and the expression level began to decrease after 24 h (FIG. 2).

Embodiment 3 Construction of NLR1-V Gene Expression Vectors

The expression vector pBI220 (Jefferson R A, Kavanagh T A. Bevan M W. GUS fusions: beta-glucuronidase as a sensitive and versatile gene fusion marker in higher plants. EMBO J. 1987, 6:3901-3907.) was used as a skeleton vector to construct the pBI220: 35S-NLR1-V vector, wherein the encoding frame of the NLR1-V in the vector was initiated by a 35S promoter, meanwhile a pBI220: Native Promoter-NLR1-V plasmid vector was constructed, wherein the encoding frame of the NLR1-V was initiated by the native promoter of the gene.

3.1 Construction of Expression Vector pBI220: 35S-NLR1-V Driven by 35S Promoter

Figure 3:
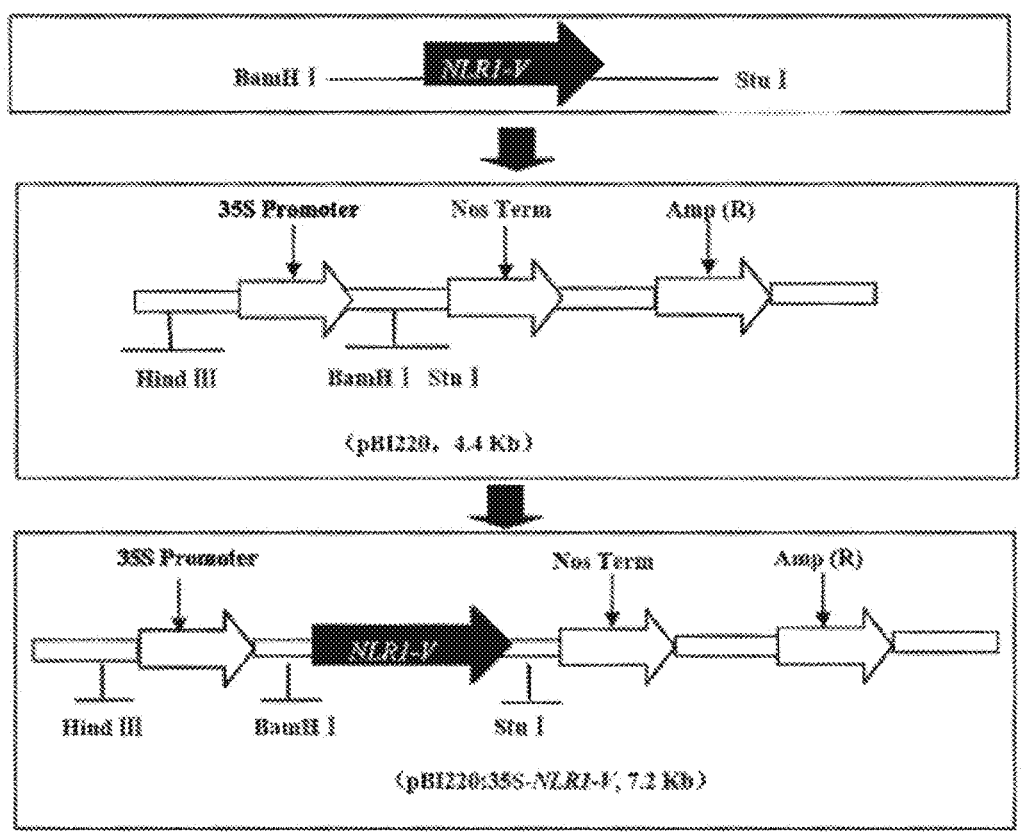
FIG. 3 illustrates expression vector maps of pBI220: 35S-NLR1-V and pBI220: Native Promoter-NLR1-V.

The NLR1-V gene cDNA cloned in Nannong 9918 induced by Bgt was used as a template, PCR amplification was performed by using primers NLR1-V-BamHI-F: GGAGAGAACACGGGGGATC-CATGTCTGCACCGGTCGTCAG (SEQ ID NO: 7) and NLR1-V-StuI-R: AACGTCGTATGGGTAAGGCCTT-TAAAGTAAAACTGGGACCACATTCATAG (SEQ ID NO: 8), and the amplified fragments were recovered. Double enzyme digestion was performed on the vector with BamHI and StuI. NLR1-V was inserted into the vector pBI220 subjected to double enzyme digestion with BamHI and StuI by a homologous recombination method (Jefferson R A, Kavanagh T A, Bevan M W·GUS fusions: beta-glucuronidase as a sensitive and versatile gene fusion marker in higher plants. EMBO J. 1987, 6:3901-3907.), and the NLR1-V was placed at the multiple cloning site behind the 35S promoter. Thus, the target gene NLR1-V was cloned downstream of the strong promoter 35S to obtain the expression vector pBI220: NLR1-V (FIG. 3A). Confirmed by sequencing, the vector was successfully constructed.

3.2 Construction of Expression Vector pBI220: Native Promoter-NLR1-V Driven by Native Promoter By introducing homologous recombination sequences at the 5' end of the primers respectively, the linearized cloning vector and the 5' end of the native promoter of NLR1-V were enabled to have mutually homologous recombinant completely identical sequences, the 3' end of the native promoter of NLR1-V and the 5' of the coding region of the NLR1-V gene were enabled to have mutually homologous recombinant completely identical sequences, and the 3' end of the coding region of the NLR1-V gene and the linearized cloning vector were enabled to have mutually homologous recombinant completely identical sequences, the linearized vector, the native promoter and the amplification product of the coding region of the NLR1-V gene were placed under the same reaction system, and the recombinant vector pBI220: Native Promoter-NLR1-V was constructed by homologous recombination.

(1) The 5' end sequence of the vector was 5'-GAT-TACGCCAAGCTT-3' (SEQ ID NO: 17), the italicized sequence is the homologous recombinant sequence recombined with Native Promoter, and the underlined sequence is shown as the HindIII recognition site. The 3' end sequence of the vector was 5'-AACGTCGTATGGGTAAGGCCT-3' (SEQ ID NO: 18), the italicized sequence is a homologous recombinant sequence recombined with the gene, and the underlined sequence is shown as a StuI recognition site.

(2) A forward amplification primer for amplifying the native promoter was NLR1-V-Native Promoter-HindIII-F: 5'-GATTACGCCAAGCTTGGTCCGTCGACTATCTCTG-3' (SEQ ID NO: 9), the italicized sequence is the sequence on the vector and the underlined sequence is shown as the HindIII recognition site for homologous recombination connection of the vector with the promoter. A reverse amplification primer for amplifying the native promoter was NLR1-V-Native Promoter R: 5'-ACCGGTGCAGACATCT-CAATGCCGAGGCTCCTTC-3' (SEQ ID NO: 10), and the italicized sequence is a genetic sequence for the homologous recombination connection of the NLR1-V gene sequence with the promoter sequence.

(3) The forward amplification primer for amplifying the coding sequence of the NLR1-V gene NLR1-V-F: 5'-TCGG-CATTGAGATGTCTGCACCGGTCGTCAG-3' (SEQ ID NO: 11), and the italicized sequence is a promoter sequence for the homologous recombination connection of the NLR1-V gene sequence with the promoter sequence. The reverse amplification primer for the coding sequence of the NLR1-V gene was NLR1-V-StuI-R: 5'-AACGTCGTATGGGTA AGGCCTAAGTAAAACTGGGACCACATTCATAG-3' (SEQ ID NO: 12), the italicized sequence is the sequence on the vector, and the underlined sequence is the restriction site of StuI for the homologous recombination connection of the NLR1-V gene with the vector.

(4) Amplification of native promoter and NLR1-V fragment

The local promoter fragment was amplified with the primers NLR1-V-Native Promoter-HindIII-F and NLR1-V-Native Promoter-R by using a high-fidelity polymerase (P Hanta® Super-Fidelity DNA Polymerase, Vazyme); the NLR1-V gene fragment was amplified with primers NLR1-V and NLR1-V-StuI-R. A 50 ul PCR reaction system: template DNA (100 ng/ul) 1 ul, 2×Phant a Max Buffer 25 ul, dNTP Mix 1 ul, positive and negative primers 2 ul each, Phanta Max Super-Fidelity DNA Polymerase 1 ul; a PCR reaction procedure: 95° C. for 30 seconds, {95° C. for 15 seconds, 56° C. for 20 seconds, 72° C. for 3 minutes} 35 cycles, 72° C. for 5 minutes. After the end of the PCR, the product by agarose electrophoresis was detected and the target band is recovered by agarose gel cutting.

(4) Recombination Reaction

The native promoter and two insertion fragments of NLR1-V were sequentially assembled and cloned by using a recombinant cloning kit (ClonExpress™MultiS One Step Cloning Kit. Vazyme). A 10 ul recombinant reaction system: 5×CE MultiS Buffer 2 ul, linearized cloning vector (88 ng) 1 ul, an insertion fragment product [native Promoter (±50 ng) 1 ul: NLR1-V (±56 ng) 1 ul]. Exnase®MultiS 1 ul. Pipetting was performed with a pipette to avoid air bubbles. A reaction was performed at 37° C. for 30 minutes. After the reaction, the reaction tube was immediately performed in an ice water bath for 5 minutes. Thus, the target gene NLR1-V was cloned downstream of the native promoter to obtain the expression vector pBI220: Native Promoter-NLR1-V (FIG. 3B). Confirmed by sequencing, the vector was successfully constructed.

Embodiment 4 NLR1-V Gene was Transferred into Wheat Leaves Using a Transient Expression Method A transient expression method is a reliable and rapid method for identifying gene functions. (Schweizer, Pokorny et al. A Transient Assay System for the Functional Assessment of Defense-Related Genes in Wheat Molecular Plant-Microbe Interactions. 1999. 12: 647-654.). In this study, the transient expression method was used to encapsulate the outer layer of metal particles with the plasmid DNA, and the metal particles and genes were bombarded into the epidermal cells of wheat leaves by means of particle bombardment. Then, the index of the Bgt haustoria bombarding the NLR1-V cells and the index of the Bgt haustoria not bombarding the NLR1-V cells were counted to determine whether the target gene has a powdery mildew resistance function.

A procedure for encapsulating the vector DNA and metal particles was as follows: tungsten powder was prepared: weighing 30 mg of tungsten powder and putting in a 1.5 ml eppendorf tube, adding 1 ml of 70% alcohol, whirling for 3-5 minutes, and standing for 15 minutes to completely precipitate the tungsten powder; discarding the supernatant after centrifugation at 12,000 rpm for 1 min; adding 1 ml of ddH$_2$O water, whirling and mixing, and discarding the supernatant (repeating three times) with centrifugation; finally, adding 500 μl of 50% glycerol and whirling and mixing for later use. Bullets were encapsulated as below: drawing 5 μl of uniformly whirled tungsten powder and putting into a 1.5 ml eppendorf tube and adding 5 μl of plasmid DNA (totally 1 μg); adding 50 μl of 2.5 M CaCl$_2$ to the eppendorf tube while swirling, then adding 20 μl of 0.1 M spermidine (currently prepared when used) and whirling for 3 minutes; after standing for 1 minute, centrifuging for 2 seconds and discarding the supernatant; adding 140 μl of 70% alcohol, whirling thoroughly, centrifuging for 2 seconds, and discarding the supernatant; then adding 140 μl of 100% alcohol, whirling thoroughly, centrifuging for 2 seconds, and discarding the supernatant; finally adding 15 μl of 100% alcohol and whirling thoroughly for later use.

When GUS gene single transformation was performed, plasmid DNA containing the GUS gene expression vector pAHC25 (Christensen A H. Quail P H. Ubiquitin promoter-based vectors for high-level expression of selectable and/or screenable marker genes in monocotyledonous plants. Transgenic Research, 1996, 5:213-218.) was encapsulated with tungsten powder; when NLR1-V was co-transformed with the GUS gene, the plasmid DNA containing the NLR1-V gene expression vector pBI220: 35S-NLR1-V was mixed with the plasmid DNA containing the GUS gene expression vector pAHC25 according to molar concentration of 1:1, and tungsten powder was encapsulated. When the GUS gene was co-transformed with the NLR1-V gene, the cell into which the marker gene GUS was transferred is also the cell into which NLR1-V was transferred. Since the cells expressed by the GUS gene were stained as completely blue, the blue cells were used as the expression cells of NLR1-V in this study.

A particle bombardment procedure was as follows: cutting the ends of leaves of wheat seedlings about 6 centimeters long, sticking them on slides in parallel, and sticking about 6 leaves per slide. Particle bombardment used a PDS 1,000/He system with a 1.350 psi splittable diaphragm and a vacuum of 28 inHg. After bombardment, the leaves were placed in a porcelain plate with wetted filter paper, covered with a preservative film with small holes, moisturized and ventilated, cultured at 18-20° C. for 4 hours, and inoculated with powdery mildew conidia at high density. After inoculation was performed for 48 hours, a GUS staining solution (formulation: 0.1 mol/L Na$_2$HPO$_4$/NaH$_2$PO$_4$ buffer (pH 7.0), containing 10 mmol/L EDTA, 5 mmol/L potassium ferricyanide and potassium ferrocyanide, 0.1 mg/ml X-Gluc, 0.1% Triton X-100, 20% methanol) was used for staining the leaves and following by vacuum infiltration for 10 minutes, incubated at 37° C. for 12 hours, and then decolorized with 70% alcohol for 2 days until the leaves turned white, and finally the Bgt spores were stained with Coomassie Brilliant Blue with a concentration of 0.6%.

Embodiment 5 Transient Expression of NLR1-V on Leaves Improved Resistance to Powdery Mildew After Bgt invades the epidermal cells of wheat leaves, the finger-shaped objects produced in the epidermal cells are called haustoria. Failure of normal generation of the haustoria is an important indicator of the resistance of leaf cells to powdery mildew. In the GUS-expressing cells, the haustoria was stained as blue by a GUS staining solution and was easily recognized under a microscope (FIG. 4). After the GUS gene was transformed into cells, the percentage (%) of the cells formed by the haustoria in the GUS-expressing cells interacting with the Bgt is the "haustoria index" (Schweizer, Pokorny et al. A Transient Assay System for the Functional Assessment of Defense-Related Genes in Wheat Molecular Plant-Microbe Interactions. 1999, 12:647-654.). The smaller the haustoria index is, the stronger the disease resistance is. This study used the "haustoria index" as a measure of disease resistance.

$$\text{Haustoria index (\%)} = \frac{GUS \text{ cells forming haustoria}}{GUS \text{ cells interacting with powdery mildew}}$$

When the GUS gene was singly transformed, the haustoria index of the susceptible wheat Yangmai 158 was 41.33% (675 interacting cells were counted), and when the GUS gene and NLR1-V co-transformed the susceptible wheat Yangmai 158, the haustoria index of cells with the expression of GUS gene (i.e. NLR1-V expression) and Bgt interaction was counted. The results showed that when NLR1-V was transferred in, the haustoria index of Yangmai 158 decreased from 41.33% to 19.23% (603 cells were counted) (FIG. 5). The results indicated that NLR1-V significantly reduces the haustoria index and has a disease-resistant effect on powdery mildew.

Embodiment 6 Silencing of NLR1-V Caused Loss of Resistance to Powdery Mildew of Powdery Mildew Resistant Variety Nannong 9918

Gene silencing was performed on NLR1-V in the disease-resistant material Nannong 9918 by using virus-induced gene silencing technology (VIGS) (Wang X Y, Cao A Z, Yu C M, Wang D W, Wang X E, Chen P D. Establishment of an effective virus induced gene silencing system with BSMV in Haynaldia villosa. Mol Biol Rep 2010, 37:967-972).

(1) Selection of silencing targets: NB-ARC and LRR domains were selected as silencing targets, and according to the sequence design of the NB-ARC and LRR domains of NLR1-V, the primers having the NB-ARC domain (NLR1-V-NBARC-F: GCTGCTAGCCGAGTGGAGGATGTGGC-TAT, SEQ ID NO: 13), NLR1-V-NBARC-R: GCTGCTAGCCGTCTGATCTTGCTTGACGA, SEQ ID NO: 14) were amplified, and the primers having the LRR domain (NLR1-V-LRR-F: GCTGCTAGCCTGAGG-GAGCTGAGGCITTA, SEQ ID NO: 15), NLR1-V-LRR-R: GCTGCTAGCCCAATCCATGTGGGAACTCT, SEQ ID NO: 16) were amplified.

(2) PCR amplification, enzyme digestion and vector construction: the plasmid containing the NLR1-V gene was used as a template, the NB-ARC domain was amplified by the NLR1-V-NBARC-F+NLR1-V-NBARC-R primer combination, the LRR domain was amplified by the NLR1-V-LRR-F+NLR1-V-LRR-R primer combination, and the target amplified fragments were recovered after gel electrophoresis. Enzyme digestion was simultaneously performed on the PCR amplification and recovery product and the γ-chain BSMV:PDS plasmid of the BSMV with NheI, and the products subjected to enzyme digestion were separately recovered and connected with T4 ligase. The products subjected to enzyme digestion with NheI of the PCR amplification product were separately inserted into the vectors subjected to enzyme digestion with NheI of the BSMV:PDS, to obtain a recombinant vector BSMV: NLR1-V$^{NB-ARC}$ targeting the NB-ARC domain and a recombinant vector BSMV: NLR1-V$^{LRR}$ targeting the LRR domain.

(3) Linearization of viral plasmids: viral vector plasmids BSMV: α, BSMV: β, BSMV: γ, BSMV: NLR1-V$^{NB-ARC}$, BSMV: PDS and BSMV: NLR1-V$^{LRR}$ were subjected to enzyme digestion and linearization. The linearized product after enzyme digestion was recovered and quantified, and transcribed in vitro with reference to RiboMAX™ Large Scale RNA Production Systems-SP6&T7 kit instructions of Promega.

(4) BSMV virus inoculation: seeds of Nannong 9918 carrying the Pm21 gene were cultured at 10-15° C., 16 hours/8 hours light/dark cycle conditions. When the second leaf of Nannong 9918 is fully unfolded, the second leaf was rubbed and inoculated with the BSMV virus; leaves inoculated with a mixture of BSMV: a, BSMV: s and BSMV: γ were used to detect whether the virus affects the phenotypic changes of Nannong 9918 interacting with powdery mildew; leaves inoculated with a mixture of BSMV: a, BSMV: s and BSMV: PDS were used to detect whether the gene silencing system is proper; and leaves inoculated with a mixture of BSMV: α, BSMV: β, BSMV: NLR1-V$^{NB-ARC}$ and BSMV: α, BSMV: β, BSMV: NLR1-V$^{LRR}$ were used to detect the effect of NLR1-V gene silencing on resistance to powdery mildew. The results showed that bleaching and viral spot symptoms began to appear on the fourth leaf of the plants inoculated with BSMV: α, BSMV: β and BSMV:PDS after the inoculation was performed for about 13-15 days. At this time, the fourth leaf inoculated with the mixture of BSMV: α, BSMV: β, BSMV: NLR1-V$^{NB-ARC}$ and BSMV: α, BSMV: β, BSMV: NLR1-V$^{LRR}$ was placed on a 6BA fresh-keeping medium, fresh powdery mildew spores were inoculated by shaking off, the incidence of the leaf was observed after the inoculation is performed for 6-8 days, at the same time, a part of the leaf was reserved for RNA extraction, and the silencing efficiency of the target gene was detected. The results showed that after the leaves infected with BSMV: NLR1-V$^{NB-ARC}$ and BSMV: NLR1-V$^{LRR}$ were inoculated with powdery mildew for 6 days, the resistance of Nannong 9918 to powdery mildew was completely lost compared with a control inoculated with BSMV: γ and BSMV: PDS. This indicates that NLR1-V plays an important role in the resistance played by Nannong 9918 (FIG. 6).

Embodiment 7 Powdery Mildew Susceptible Varieties Introduced with NLR1-V Improved the Resistance to Powdery Mildew The NLR1-V gene was transferred into a powdery mildew susceptible variety Yangmai 158 and a susceptible mutant NM14 by particle bombardment transformation. A transformation method was as follows: 1, picking up about 2,000 pieces of Yangmai 158 embryogenic calli pre-cultured for 7 days, and pretreating the embryogenic calli in a hypertonic medium [MS+(0.5 mg/L ABA)+(500 mg/L hydrolyzed casein)+(2 mg/L 2,4-D)+(30 g/L glucose)+(0.4 mol/L mannitol), pH5.8] for 4-5 hours; 2, transforming the expression vectors pBI220: 35S-NLR1-V and pBI220: Native Promoter-NLR1-V carrying the targeted gene of NLR1-V into calli of the Yangmai 158 and the susceptible mutant NM14 by particle bombardment (in the transformation process, the vector pAHC-20 containing a screening marker Bar gene is used as a co-transformation vector), and after bombardment, culture was continued for 16 hours on the hypertonic medium; 3, the calli were transferred to a recovery medium [(½MS)+(500 mg/L hydrolyzed casein)+(2 mg/L 2,4-D)+(30 g/L sucrose), pH 5.8] and dark culture was performed for 2 weeks; 4, the calli were transferred to a screening medium containing herbicide [(½MS)+(0.5 mg/L ABA)+(500 mg/L hydrolyzed casein)+(1 mg/L 2,4-D)+(30 g/L sucrose)+(4 mg/L Bialaphos), pH 5.8] and screening culture was performed for 2 weeks; 5, resistant calli were transferred to a differential medium [(½MS)+(1 mmol/L L-glutamine)+(200 mg/L hydrolyzed casein)+(1 mg/L KT)+(0.5 mg/L IAA)+(30 g/L sucrose)+(0.8% agar), pH 5.8] for differentiation, and when the differentiated shoots grew to 2-4 centimeters, the shoots were transferred to a rooting medium [(½MS)+(1 mg/L KT)+(30 g/L sucrose)+(0.8% agar), pH 5.8]; 6, when the regeneration seedlings were about 8 centimeters long and the root systems were stronger, the tube was opened for hardening the seedlings for 1-2 days, and finally, the medium residue carried by the root systems were washed and the seedlings were transplanted into a pot.

The identification of resistance to powdery mildew in a seedling stage was carried out by an in-vitro identification method. The specific method was as follows: cutting the leaves of the regeneration plants with same growth, placing the leaves neatly on the 6-BA fresh-keeping medium, inoculating the leaves with the spores of fresh Bgt by shaking off, and observing the incidence of the leaves after the inoculation was performed for 6 days. The results showed that the NLR1-V gene was transferred to the Yangmai 158 and the susceptible mutant under the initiation of 35S and native promoter, and some of the positive transgenic plants were immune to wheat powdery mildew (FIG. 7).

What is claimed is:

1. An NLR1-V gene comprising SEQ ID NO: 1.

2. A method of increasing the resistance of a wheat plant to powdery mildew, said method comprising:
    transforming a construct comprising the NLR1-V gene of claim 1 operably linked to a plant promoter into a wheat plant, thereby producing a wheat plant with increased resistance to powdery mildew.

3. A recombinant expression vector comprising the NLR1-V gene of claim 1 under control of a promoter.

4. The recombinant expression vector of claim 3, wherein the promoter is a 35S promoter.

5. The recombinant expression vector of claim 3, wherein the recombinant expression vector is a plasmid and the NLR1-V gene is inserted between restriction sites within the plasmid.

6. The recombinant expression vector of claim 5, wherein the restriction sites are BamHI and StuI restriction sites.

7. A wheat variety comprising the NLR1-V gene of claim 1, wherein the wheat variety is resistant to powdery mildew.

8. A wheat variety comprising the recombinant expression vector of claim 3, wherein the wheat variety is resistant to powdery mildew.

* * * * *